United States Patent [19]

Blum

[11] Patent Number: 4,804,474

[45] Date of Patent: Feb. 14, 1989

[54] ENERGY EFFICIENT DIALYSIS SYSTEM

[76] Inventor: Robert Blum, 364 Maple Ave., Harleysville, Pa. 19438

[21] Appl. No.: 131,016

[22] Filed: Dec. 10, 1987

[51] Int. Cl.$^4$ .............................................. B01D 13/00
[52] U.S. Cl. .................................... 210/641; 210/259; 210/321.66
[58] Field of Search ...................... 210/138, 96.2, 259, 210/641, 181, 188, 321.66

[56] References Cited

U.S. PATENT DOCUMENTS

| | | | |
|---|---|---|---|
| 3,827,561 | 8/1974 | Serfass et al. | 210/180 |
| 3,827,975 | 8/1974 | Bizot et al. | 210/22 |
| 3,878,095 | 4/1975 | Frasier et al. | 210/87 |
| 4,072,610 | 2/1978 | Gow et al. | 210/96.2 X |
| 4,338,190 | 7/1982 | Kraus et al. | 210/195.2 |
| 4,366,051 | 12/1982 | Fischel | 210/96.2 |
| 4,477,342 | 10/1984 | Allan et al. | 210/87 |

Primary Examiner—Frank Spear
Attorney, Agent, or Firm—Dann, Dorfman, Herrell & Skillman

[57] ABSTRACT

An energy efficient dialysis system which requires a minimal amount of energy to operate and maintains critical operating temperatures for effective reverse osmosis and dialysis. The system includes a hot fluid inlet for causing a flow of washing fluid, a reverse osmosis machine for receiving the flow of washing fluid at a first given temperature to filter the washing fluid and discharge impurities in a discharge stream, a plurality of kidney machines receiving the filtered washing fluid to remove contaminants from a body fluid at a second given temperature, a heater adjacent to the entry of the kidney machine to change the temperature of the filtered washing fluid from the first given temperature to the second given temperature, and a valve to control the temperature of the washing fluid entering the reverse osmosis machine; an energy conserving apparatus comprising a heat exchanger for receiving the discharge streams from the reverse osmosis and kidney machines and a cold fluid inlet to introduce fresh washing fluid through the heat exchanger.

17 Claims, 1 Drawing Sheet

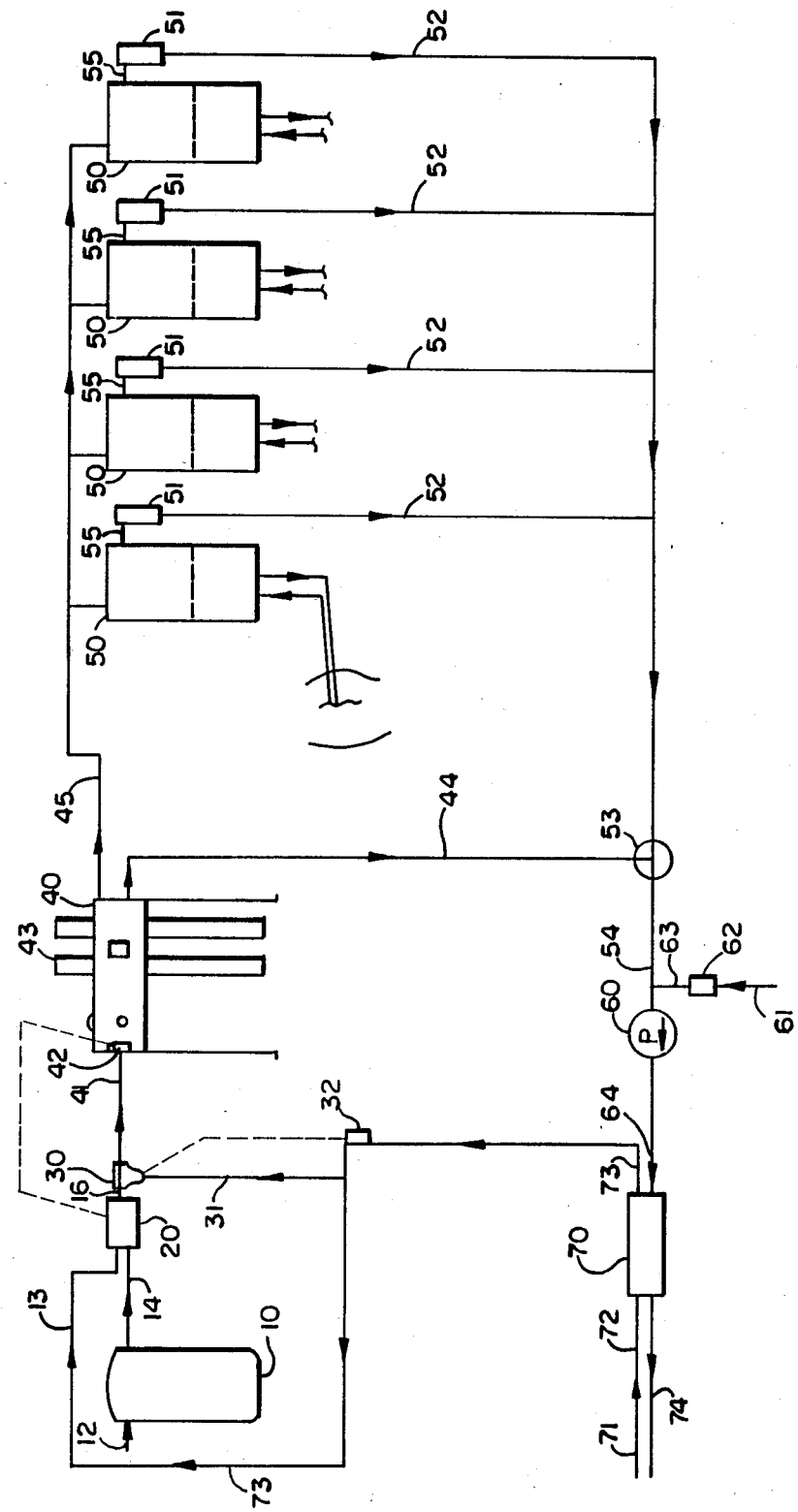

ENERGY EFFICIENT DIALYSIS SYSTEM

FIELD OF THE INVENTION

The invention relates to the field of dialysis systems of the type which utilize heat exchangers and recycle streams to preheat a washing fluid to a suitable temperature for reverse osmosis and dialysis. In particular, the invention relates to a system which utilizes a bypass stream, drainage streams and a heat exchanger to preheat the washing fluid and thereby achieve a high degree of energy conservation while maintaining critical operating temperatures for reverse osmosis and dialysis.

BACKGROUND OF THE INVENTION

For the treatment of kidney disfunction, it is common practice to use a dialysis system to remove impurities from the patient's blood that would otherwise be removed by a healthy pair of kidneys. The dialysis systems commonly take the form of a process having the steps of drawing a washing fluid such as water through an inlet to the system, heating the washing fluid to suitable temperatures for effective dialysis and filtration such as reverse osmosis, passing the washing fluid through a filter to remove impurities therefrom and, finally, passing the washing fluid through the dialysis system for use in the kidney machines wherein contaminants from the patient's blood are deposited in the washing fluid which is disposed of by way of a fluid outlet. While the process of dialysis may be effectively achieved through this system, a large quantity of heat energy is required to heat the inlet washing fluid to suitable temperatures for effective filtration and dialysis.

Other systems additionally utilize a heat exchanger and recycle stream to preheat the inlet washing fluid to suitable temperatures for optimal filtration. In effect, the heated contaminated washing fluid, after exiting from the dialysis step of the process, is passed through a heat exchanger adjacent to a washing fluid inlet; thereby utilizing the heat energy from the contaminated washing fluid to preheat the inlet washing fluid toward the critical operating temperature necessary for effective filtration. While some energy conservation is achieved by using a heat exchanger, a large quantity of energy may still be lost throughout the system and the heating step of the dialysis system is still burdened to warm the inlet fluid to a suitable temperature for optimal filtration.

SUMMARY OF THE INVENTION

In an attempt to overcome these problems, the dialysis system of the present invention has been designed to include multiple drainage streams, a bypass stream and blending junctions with electronic monitoring and control apparatus to minimize the input heat energy required to effectively operate the system by utilizing the heat energy from the drainage streams of various steps in the dialysis system. When the dialysis system is operated, not only is a minimum amount of energy required but also a critical temperature and uniform pressure for effective filtration and dialysis may be maintained throughout the system.

The present invention provides a dialysis system which maintains suitable temperatures for effective filtration and dialysis while requiring a minimal amount of energy to the washing fluid inlet heater in order to maintain the critical system temperature.

In addition, the present invention provides a dialysis system having a configuration which advantageously permits the effective dialysis of a patient's blood at a minimal operating cost to both the patient and the health care institution.

Furthermore, the present invention provides a dialysis system having a configuration which utilizes the heat energy not only from the drainage stream of the dialysis step but also the drainage stream from the reverse osmosis step to preheat the inlet washing fluid using a heat exchanger.

Additionally, the present invention provides a dialysis system having a configuration which utilizes mutiple streams from the heat exchanger energy recycle stream and electronic thermal sensing means to regulate the mixture of fluids and thereby maintains critical temperatures for effective reverse osmosis and dialysis.

Also, the present invention provides a dialysis system having a configuration which utilizes a pump between the heat exchanger and the kidney machines to maintain an equal flow rate throughout the system thereby preventing the development of back pressure.

The present invention provides a dialysis system which comprises the steps of preheating the inlet washing fluid, reverse osmosis, dialysis and heat exchange with the inlet washing fluid while maintaining critical temperatures in the washing fluid for effective reverse osmosis and dialysis.

The preferred embodiment of the invention includes a hot fluid inlet for causing a flow of water, a reverse osmosis machine for receiving the flow of water and having a membrane operable at a first given temperature to filter the water and discharge impurities therefrom in a discharge stream, a plurality of kidney machines receiving the filtered water from the reverse osmosis machine and having a membrane operable to remove contaminants from a body fluid by entraining the contaminants in the flow of water at a second given temperature, a heater adjacent to the entrance of the kidney machine to change the temperature of the filtered water from the first given temperature to the second given temperature, and a valve to control the temperature of the water entering the reverse osmosis machine at the first given temperature; and apparatus for conserving energy which comprises a heat exchanger for receiving the discharge streams from the reverse osmosis machine and the kidney machines, a cold fluid inlet to introduce fresh water through the heat exchanger to recover heat energy from the discharge streams to preheat the cold water, and a blending valve to introduce the preheated washing fluid into the hot fluid inlet stream to obtain water at the first given temperature for introduction into the reverse osmosis machine.

BRIEF DESCRIPTION OF THE DRAWINGS

The foregoing summary as well as the following detailed description of a preferred embodiment of the present invention, will be better understood when read in conjunction with the appended flow diagram, in which:

The FIGURE is a schematic diagram of a dialysis system showing the processing of wash water as it flows from the fluid inlets to the drain.

DESCRIPTION OF THE PREFERRED EMBODIMENT

Referring now to the drawing, there is shown generally an energy efficient dialysis system including a cold water inlet 71, and a hot water inlet 12 for causing a flow of a washing fluid such as water into the dialysis system, a heater 10 to heat the flow of water from the hot water inlet 12, means to control the temperature of the water, hereinafter referred to as blending valves 20 and 30, a reverse osmosis machine 40 for receiving the flow of heated water at a first given temperature to filter the water and discharge impurities therefrom, a plurality of kidney machines 50 for receiving the filtered water from the reverse osmosis machine to remove contaminants from a body fluid and apparatus for conserving energy which comprises a heat exchanger 70 for receiving the discharge streams from the reverse osmosis machine and the kidney machine to preheat the water for entry to the reverse osmosis machine 40.

Referring now to the figure, the heater 10 heats the flow of water entering the dialysis system through the hot fluid inlet 12, the hot water inlet line, discharges the heated water in a hot water stream 14 and finally to a blending valve 20 where the hot water is blended with a flow of water 73 from the cold fluid inlet 71, the cold water inlet line, which has been preheated by the heat exchanger 70. In the present instance, the hot water heater 10 is of the electric type. The blending valve 20 is controlled by a thermal sensor 41 downstream and adjacent to an inflow port 42 of the reverse osmosis machine 40. When the temperature of the water falls below the critical temperature of 77° F., hereinafter the first given temperature, the thermal sensor 41 actuates the blending valve 20 such that the heated flow of water from the hot water inlet line is increased relative to the preheated flow of water 73 from the cold water inlet line 71.

In addition, when the temperature of the water from the hot water inlet 12 rises above the first given temperature, the thermal sensor 41 actuates the valve 30 to add a bypass stream 31 from the cold water inlet 71 preheated by the heat exchanger 70 directly to the valve 30 where the temperature is modulated to achieve the aforesaid first given temperature. It is essential that the temperature of the water remain at 77° F. for optimal operation of the reverse osmosis machine 40.

The reverse osmosis machine 40 receives the flow of hot water from the blending valves 20 and 30 to purify the water and discharge impurities therefrom in a drainage stream 44. The reverse osmosis machine 40 includes a membrane 43 to filter the water emptying the purified water into a product stream 45. Approximately 50% of the water is discharged to the drainage stream 44 and the other 50% of the water continues on into the product stream 45 for use in the kidney machines 50.

After entrance into the product stream 45, the water enters the kidney machines 50 where the temperature of the water is stepped up to 100° F., the second given temperature, using an internal 2000 watt heater, for example. Next, the hot water is mixed with a dialysate fluid and enters an artificial kidney 51 through discharge stream 55. In the artificial kidney 51, the blood from a patient and the dialysate-water mixture pass in opposite directions along the surface of a membrane and impurities are thereby removed from the blood by osmosis. The impurities removed from the patient's blood are entrained in the dialysate washing fluid and are discharged from each artificial kidney 51 through a drainage stream 52. Each kidney machine 50 includes an artificial kidney 51 and an intake and exhaust port for receiving blood from a patient whereby the blood is purified by the artificial kidney and returned to the patient's body.

The apparatus for conserving energy comprises a heat exchanger 70 for receiving the discharge streams 44 and 52 from the reverse osmosis machine 40 and the kidney machines 50, respectively. The discharge streams 44 and 52 are combined by a mixing means, hereinafter referred to as mixing point 53, to form a contaminated discharge stream 54. After the contaminated discharge stream 54 passes through the pump 60, it is discharged into a contaminated discharge stream 64. The contaminated discharge stream 64 passes into heat exchanger 70 where it passes in effective heat exchange relationship with a stream 72 of water from the cold water inlet 71 such that the stream 72 absorbs heat energy from the contaminated discharge stream 64. After the heat energy from the contaminated discharge stream 64 has been absorbed through the heat exchange, the contaminated discharge stream passes out of the system through a fluid outlet 74. A preheated stream 73 exits from the heat exchanger 70 for addition to a flow of water from the hot water inlet 12 for mixing at blending valve 20.

If the preheated stream 16 exceeds the first given temperature, a thermal switch 32 is actuated by thermal sensor 41 and thermal switch 32 diverts the stream 73 through a bypass line 31 for addition to stream 16 at blending valve 30, so as to maintain the water temperature at the port 42 at 77° F.

A pump 60 is located between the mixing point 53 and heat exchanger 60 to control the flow of the contaminated discharge stream 54 through the heat exchanger 70. The pump 60 continues the movement of the washing fluid and maintains a uniform flow rate throughout the dialysis system to ensure that a back pressure does not develop at heat exchanger 70. The pump 60 is preferably a positive displacement type pump.

The discharge fluid from the pump 60 enters a contaminated drainage stream 64. As an example, the discharge water may enter the heat exchanger 70 at a temperature of approximately 85° F. Entering the opposite side of heat exchanger 70 is incoming water, such as city water, from the cold water inlet 71 at approximately 55° F. Through thermal conduction in the heat exchanger, heat energy is transferred from the discharge water at 85° F. to the incoming water at 55° F., thereby raising the temperature of the incoming water to approximately 75° F.

Before the preheated water 73 reaches the critical temperature at the sensor 41, it is directed on to the blending valve 30 where it is added to a hot water stream 14 from the hot water inlet 12, when needed, to maintain the temperature of the water to the reverse osmosis machine 40 at 77° F.

Between the pump 60 and the mixing point 53, a 24-hour timer and valve, hereinafter referred to as flushing means 62, permits a washing fluid such as water to enter the heat exchanger 70 of the dialysis system for ten-minute intervals once every 24 hours to prevent the buildup of corrosive material in the heat exchanger 70. The water enters the flushing means 62 through a fluid inlet 61 for entrance to the heat exchanger.

Some of the many advantages and novel features of the invention should now be apparent in view of the foregoing description and accompanying drawings. For example, a conventional dialysis system has been described which consists of fluid inlets for causing a flow of water, a reverse osmosis machine for receiving the flow of water and having a membrane operable at a first given temperature to purify the water and discharge impurities therefrom in a discharge stream, a plurality of kidney machines receiving the filtered water from the reverse osmosis machine and having a membrane operable to remove contaminants from a body fluid by entraining the contaminants in the flow of water at a second given temperature, a heater, preferably positioned internally adjacent to the entry of the kidney machine, to change the temperature of the filtered water from the first given temperature to the second given temperature, and a valve to control the temperature of the water entering the reverse osmosis machine at the first given temperature. The improved apparatus for conserving energy comprises a heat exchanger for receiving the discharge streams from the reverse osmosis machine and the kidney machines, and a cold fluid inlet to introduce fresh water through the heat exchanger to recover heat energy from the discharge streams to preheat the water. By using the method and apparatus of the invention, the energy reguired to operate the hot water heater is substantially curtailed, thus resulting in significant savings in the cost of operating a dialysis system.

It will be recognized by those skilled in the art that changes or modifications may be made to the above-described embodiment without departure from the broad inventive concepts of the invention. For example, aside from mixing the hot and cold water streams 14 and 73, respectively, at blending valve 20; hot water stream 14 and bypass stream 31 could be mixed at blending valve 20 utilizing the preheated cold water stream 73 to lower the temperatures of stream 16 to the critical temperature, when desired, at blending valve 30. Furthermore, pump 60 may be effectively placed downstream of heat exchanger 70 adjacent to fluid outlet 74 to maintain a uniform flow rate throughout the dialysis system and eliminate blackflow. It is understood, therefore, that the invention is not limited to the particular embodiment which is disclosed, but is intended to include all modifications and changes which are within the scope and spirit of the invention as defined by the appended claims.

I claim:

1. In a dialysis system having fluid inlet means for causing a flow of washing fluid, a reverse osmosis machine receiving said flow of washing fluid and having a membrane operable at a first given temperature to filter said washing fluid and discharge impurities therefrom in a discharge stream, at least one kidney machine receiving the filtered washing fluid from said reverse osmosis machine and having a membrane operable to remove contaminants from a body fluid by entraining said contaminants in said flow of washing fluid at a second given temperature, heating means adjacent the entry of said kidney machine to change the temperature of said filtered washing fluid from said first given temperature to said second given temperature, and means to control the temperature of the washing fluid entering the reverse osmosis machine at said first given temperature; apparatus for conserving energy comprising heat exchange means receiving the discharge streams from said reverse osmosis machine and said kidney machine, means to introduce fresh washing fluid through said heat exchanger to recover heat energy from said discharge streams to preheat the washing fluid, and means to introduce said preheated washing fluid into said fluid inlet means to obtain washing fluid at said first given temperature for being received into said reverse osmosis machine.

2. Apparatus according to claim 1 including means to mix the discharge streams from the reverse osmosis machine and the kidney machine to form a contaminated fluid discharge flow in advance of said heat exchanger, and pump means to control the flow of said contaminated fluid discharge flow through said heat exchanger.

3. Apparatus according to claim 1 wherein said fluid inlet means includes a cold water inlet line, a hot water inlet line and a blending valve to mix said cold and hot water to produce washing fluid having said first given temperature.

4. Apparatus according to claim 3 including thermal sensing means adjacent the inlet of said reverse osmosis machine and connected to said blending valve to control the temperature of the washing fluid entering the reverse osmosis machine.

5. Apparatus according to claim 4 wherein said heat exchanger is connected to feed preheated water into said inlet means upstream of said blending valve.

6. Apparatus according to claim 5 including a bypass connecting said heat exchanger to said inlet means downstream of said blending valve, said bypass means including valve means and a thermal sensor operable to afford flow through said bypass into said inlet means when said preheated water is at a temperature above said first given temperature.

7. Apparatus according to claim 1 wherein said hot water inlet line includes an electric heater responsive to the demand from said blending valve to heat water to generate hot water.

8. Apparatus according to claim 1 including a plurality of said kidney machines, said mixing means operable to combine the discharge streams from all of said plurality of kidney machines with the discharge stream from said reverse osmosis machine.

9. Apparatus according to claim 1 including means to introduce flushing liquid through said heat exchanger to flush out any contaminants deposited therein, and timer means operable to periodically actuate said flushing means for predetermined intervals.

10. A method of conserving energy in a dialysis system having fluid inlet means for causing a flow of washing fluid, a reverse osmosis machine receiving said flow of washing fluid and having a membrane operable at a first given temperature to filter said washing fluid and discharge impurities therefrom in a discharge stream, at least one kidney machine receiving the filtered washing fluid from said reverse osmosis machine and having a membrane operable to remove contaminants from a body fluid by entraining said contaminants in said flow of washing fluid at a second given temperature, heating means adjacent the entry of said kidney machine to change the temperature of said filtered washing fluid from said first given temperature to said second given temperature, and means to control the temperature of the washing fluid entering the reverse osmosis machine at said first given temperature; the steps comprising providing heat exchange means, directing the discharge streams from said reverse osmosis machine and said kidney machine into said heat exchange means, introducing fresh washing fluid through said heat exchanger to recover heat energy from said discharge streams to preheat the washing fluid, and introducing said preheated washing fluid into said fluid inlet means to obtain washing fluid at said first given temperature for being received into said reverse osmosis machine.

11. The method according to claim 10 including the steps mixing the discharge streams from the reverse osmosis machine and the kidney machine to form a contaminated fluid discharge flow in advance of said heat exchanger, and controlling the flow of said contaminated fluid discharge flow through said heat exchanger.

12. The method according to claim 10 wherein said fluid inlet means includes a cold water inlet line and a hot water inlet line, including the step of blending the flows from said cold and hot water inlet lines to produce washing fluid having said first given temperature.

13. The method according to claim 12 including the step of thermally sensing the fluid adjacent the inlet of said reverse osmosis machine and controlling said blending step to control the temperature of the washing fluid entering the reverse osmosis machine.

14. The method according to claim 12 wherein said heat exchanger is connected to said cold water inlet including the step of preheating the water of said cold water inlet upstream of said blending step.

15. The method according to claim 12 including the step of bypassing said hot water inlet line and connecting said heat exchanger to said inlet means downstream of said blending step, said bypassing step including controlling the flow of preheated washing fluid in response to the temprature thereof to afford flow through said bypass into said inlet means when said preheated water is at a temperature above said first given temperature.

16. The method according to claim 11 including the step of mixing the discharge streams from all of a plurality of said kidney machines with the discharge stream from said reverse osmosis machine.

17. The method according to claim 10 including the step of introducing a flushing liguid through said heat exchanger to flush out any contaminants deposited therein, and periodically actuating said flushing step for predetermined intervals.

* * * * *